United States Patent [19]
Lambert

[11] 4,393,865
[45] Jul. 19, 1983

[54] NAPKIN FOR A YOUNG CHILD

[76] Inventor: Jacques Lambert, 29 rue de la Gare, 59232 Vieux-Berquin (Nord), France

[21] Appl. No.: 272,756

[22] Filed: Jun. 11, 1981

[30] Foreign Application Priority Data

Oct. 15, 1980 [FR] France .............................. 80 22520
Dec. 20, 1980 [FR] France .............................. 80 27989

[51] Int. Cl.³ .............................................. A61F 5/00
[52] U.S. Cl. ................................. 128/80 A; 128/87 C
[58] Field of Search ...................... 128/80 A, 87 C, 78

[56] References Cited

U.S. PATENT DOCUMENTS 2,935,984  5/1960  Kerr .................................. 128/87 C
3,114,368 12/1963  Richmond ........................ 128/80 A

FOREIGN PATENT DOCUMENTS 1240222  5/1967  Fed. Rep. of Germany .... 128/87 C

*Primary Examiner*—J. Yasko
*Attorney, Agent, or Firm*—Robert E. Burns; Emmanuel J. Lobato; Bruce L. Adams

[57] ABSTRACT

A napkin for a young child, intended to prevent or cure an abnormality of one or both hips, such as dysplasia or subluxation of the hip. The napkin is characterized by the fact that it comprises semi-rigid means for the orientation of the child's thighs in a bent position approximately at 90° with respect to the pelvis and in an abduction position at 60° approximately, and flexible retaining means shaped and positioned on the child's body to apply and retain the orientation means on the child's thighs and pelvis and vice versa. The orientation means may be of the ischial-sacral type and are constituted by a cross-member, by a cushion. Alternatively, the orientation means are of the ischial-pubic type and are constituted by a cushion, whereof the front end is engaged between the child's thighs.

16 Claims, 8 Drawing Figures

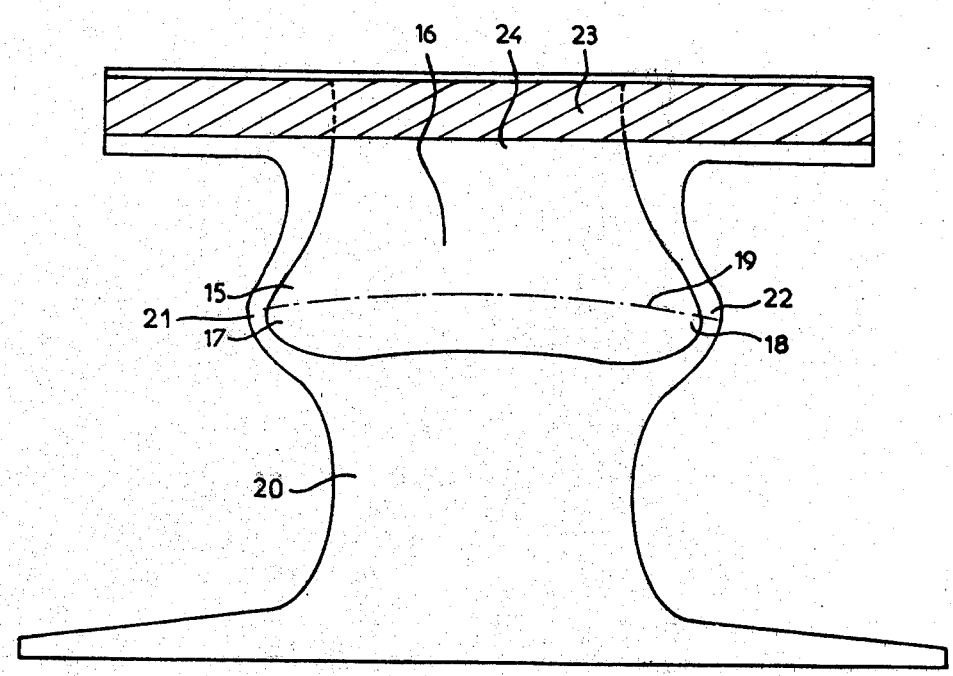
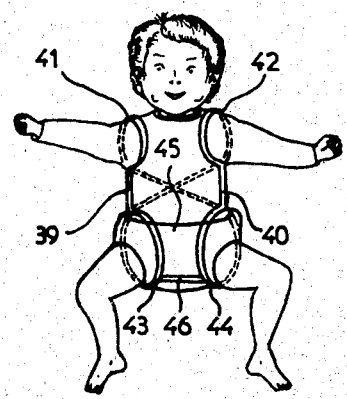
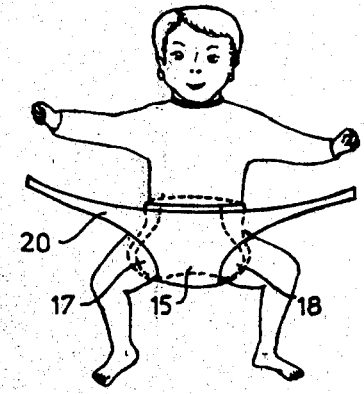

NAPKIN FOR A YOUNG CHILD

The invention relates to a napkin for a young child and more particularly for a child of less than approximately four months old and in any case for a child who is not yet able to walk.

The napkin according to the present invention is intended to prevent or cure an abnormality of either or both of the child's hips, such as dysplasia or subluxation of the hip. When born, a child may have abnormalities of this type in one hip or in both hips or the latter may appear sometime after he is born. It is possible to detect them by a clinical and radiological examination and generally they are not of great importance when treated successfully as soon as they are diagnosed.

Means of treatment which are currently in existence consist of keeping the child's thighs in a so-called abduction position, i.e. separated from each other and bent with respect to the pelvis.

Two types of current existing arrangement make it possible to keep the child's thighs in such a position. There are firstly rigid arrangements which are placed over the child's clothes, such as for example Becker pants, the Pavlick harness and Von Rozen splints. Rigid arrangements of this type have the major drawback of keeping the child's limbs in an unnatural position, from which may result more or less serious cases of osteochondritis. Furthermore, taking into account the morphology of the child, positioning and adjustment of these arrangements are particularly difficult and should be attended to by experts. They are thus difficult to use, in particular for a mother.

Another type of arrangement for reducing the danger of irreversible lesions such as osteochondrities, uses more flexible materials, such as cotton napkins, possibly comprising a special cut-out, superimposed traditional layers etc. By way of example it is possible to mention a method for binding a child in its napkin, known under the same of the Saint-Vincent de Paul method. With arrangements of this type, the child's thighs are kept in position by superimposing traditional napkins and/or by placing rolled napkins between the child's thighs.

The fitting of such arrangements is thus relatively complicated, in view of the fact that they utilize several independent components, which it is necessary to position one with respect to the other and with respect to the child's body.

Furthermore, currently existing arrangements are placed above the child's clothing or traditional napkin.

It should also be noted, in a general manner, that keeping the child's thighs in the so-called abduction position should be permanent, at least until the abnormalities of its hips disappear. Currently existing arrangements are thus difficult to use for the child's mother and are relatively bulky.

They also have a considerable drawback for the child's mother from the psychological point of view. In fact, they have an imposing and generally repulsive appearance, which is in all cases disproportionate to the apparent seriousness of the abnormality of the child's hips.

Furthermore, currently existing arrangements have a curative characteristic and owing to their complexity, cannot be used as a preventive measure. In fact, it should be noted that binding a child with a napkin in the so-called abduction position from his birth even if an abnormality of one of his hips is not diagnosed, may prevent the development of such abnormalities and above all is completely harmless for a child having normal hips.

Thus, one of the objectives of the present invention is to propose a napkin mainly having a preventive characteristic with regard to an abnormality of the hips of a new born baby, but also a curative characteristic.

Another objective of the present invention is to propose an arrangement which is particularly simple to position on the child, even for a mother without special medical knowledge.

Another objective of the present invention is to propose an arrangement which is not bulky and which may be placed below the child's clothing or combined with the latter, which from a psychological point of view facilitates its use.

Another objective of the present invention is to propose an arrangement which in particular does not completely impede the movement of the child's thighs and which does not keep the latter in an unnatural position.

Another objective of the present invention is to propose an arrangement which is advantageously suitable for mass manufacture and which complements or can be combined with currently existing napkins, such as triangular napkins, nappy pants, disposable nappies.

Other objectives and advantages of the present invention will become apparent from the ensuring description, which is nevertheless given solely by way of example and is not intended to limit the latter.

The napkin for a young child, intended to prevent or cure an abnormality of one or both hips, such as dysplasia, subluxation of the hip, a reduceable and stable dislocation by binding the child in a napkin in the abduction position, is characterised by the fact that it comprises semi-rigid means for the orientation of the child's thighs, in a bent position at an angle of approximately 90° with respect to the pelvis and in an abduction position at an angle of approximately 60°, which flexible retaining means shape and position on the child's body, by pressing and retaining these orientation means on the child's thighs and pelvis and vice versa.

The invention will be better understood on referring to the ensuing description and to the accompanying drawings which form an integral part thereof.

FIG. 3 shows diagrammatically certain constituent parts of the napkin, in another non-limiting embodiment of the invention.

FIG. 4 shows a child bound with the arrangement of FIG. 3.

FIG. 8 shows diagrammatically a variation of the retaining means according to the invention.

The term "napkin" which is used in this instance generally designates any arrangement intended to wrap around young children below the waist. This term should thus be understood in a wide sense.

The napkin according to the present invention comprises orientation means and retaining means. However, as will become apparent hereafter, according to each individual case, it may also comprise other means, such as means for absorbing the child's excrement, sealing means, means intended to prevent the irritation of the child's skin etc.

Furthermore, hereafter, for the various means, the term "longitudinal" qualifies the direction extending from the front part towards the rear part of the napkin and vice versa. The term "transverse" qualifies a direction substantially at right angles to the longitudinal direction.

Figure 1:
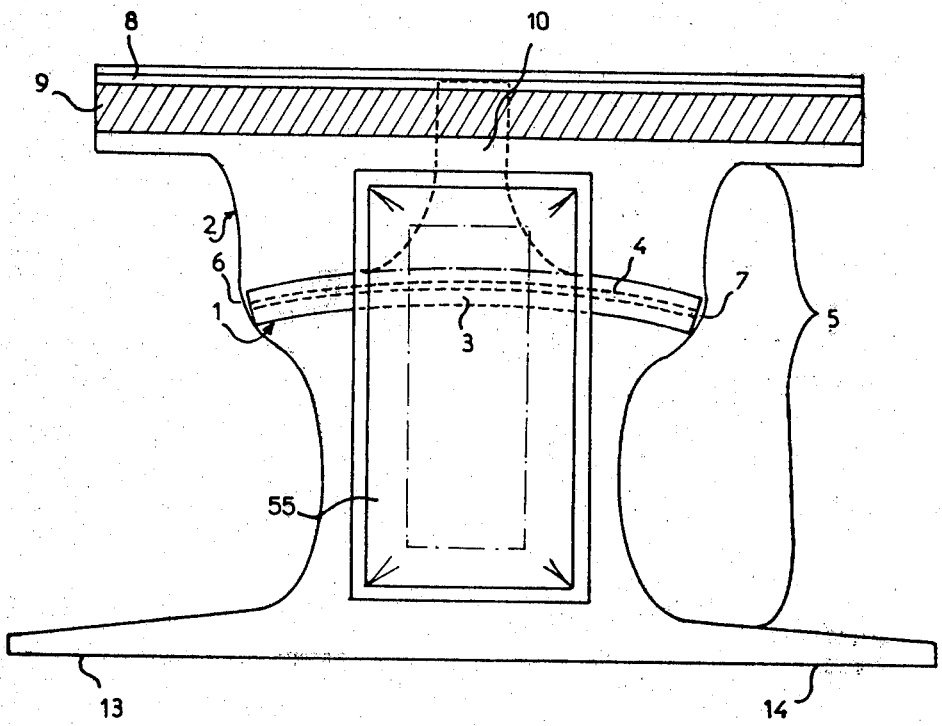
FIG. 1 shows diagrammatically certain constituent parts of the napkin according to the present invention, in a non-limiting embodiment of the latter.
Figure 2:
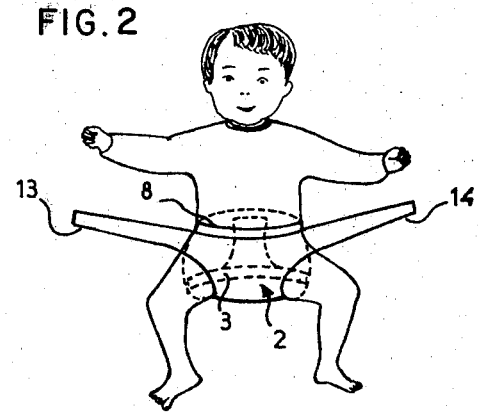
FIG. 2 shows a child bound with the arrangement shown diagrammatically in FIG. 1.

FIGS. 1 and 2 illustrate the present invention in a non-limiting embodiment of the latter. In particular these figures show orientation means 1 and retaining means 2. The orientation means 1 are substantially symmetrical with respect to a longitudinal axis.

The orientation means 1 are mainly constituted by a cross-member 3 of semi-rigid or possibly rigid material, which extends transversely with respect to the napkin. Preferably, the cross-member 3 is curved, along a curve which corresponds substantially to the angle of opening of the child's thighs which one wishes to obtain. Also, its cross-section, which may be of any suitable shape and for example rectangular, elliptical or oval is very flat, its largest dimension being located substantially in the plane of FIG. 1.

Furthermore, the length of the cross-member 3 is determined in order that when the napkin is in position on the child, the backs of his thighs rest thereon. Thus, this length is equal to or slightly less than the distance separating the child's knees, when his thighs are in the desired position.

The semi-rigidity or possibly the rigidity of the cross-member 3 is attained by making this cross-member from a semi-rigid or rigid material, or by reinforcing the latter with a rib 4.

The napkin according to the present invention also comprises retaining means 2. In FIG. 1, these means are shown diagrammatically by a traditional napkin, of any suitable material and for example of washable polyvinyl chloride.

The central area 5 of the retaining means may be constituted by a sheet or an envelope inside which are inserted the orientation means 1. This central area has a known shape, adapted to the morphology of the child. However, preferably, as shown diagrammatically in FIG. 1, it comprises two "projections" 6 and 7, in the vicinity of each end of the cross-member 3.

In their upper or rear part and in their lower or front part, the retaining means also comprise means for securing the napkin to the child's body. As they are shown diagrammatically in FIG. 1, for the upper or rear part, these securing means consist of a belt 8, possibly reinforced by a substantially non-extensible flexible tape 9. At each of its ends, the belt 8 comprises additional fasteners, such as adhesive means, means known by the name of velcro tapes etc., which preferably make it possible to adjust the length of the belt.

Furthermore, in the area which will be applied against the child's navel, the belt could comprise a compress, not shown in FIG. 1, intended to ensure the retention of the umbilical cord orifice in position.

In a preferred embodiment, the cross-member 3 is positioned and retained with respect to the belt 8 by a strip 10 which connects them one to the other.

In the embodiment illustrated in FIG. 1, in their lower or front part, the retaining means comprise two tapered lateral ends 13 and 14, suitable for facilitating securing this end of the napkin by knotting on the child's back, or by adhesive or other means.

Other means for securing the retaining means could be used in place of the belt 8 and the tapered lateral ends 13 and 14 and for example an arrangement of the braces type.

As has been mentioned previously, the napkin may comprise other means and for example absorption means, constituted by an absorbent pad 55 disposed in the vicinity of the central part of the napkin. The pad 55 may be integrated in the retaining means and connected to the latter for example by welding or sticking. In this case, the absorbent pad is located above the cross-member 3.

FIG. 2 shows a child bound with the arrangement of FIG. 1. The belt 8 of the retaining means 2 has been closed around the child's waist, the central area 5 has been pulled forcefully by causing the latter to pass between the child's legs. It remains solely to knot the tapered lateral ends 13 and 14 on the child's back, around his waist. These various operations bring the cross-member 3, more precisely its ends, into contact with the rear parts of the child's thighs. The retaining means press the cross-member against the child's thighs and vice versa, thus orientating the thighs substantially parallel to the ends of the cross-member.

The child's thighs are thus orientated and retained in a so-called abduction position. This position may be defined by the bending of the thighs at approximately 90° with respect to the pelvis and an opening of the latter of approximately 120°, i.e. respectively separated by approximately 60° with respect to the position in which they are together.

It should be noted that in the case of the present arrangement, the child's thighs are not placed in an unnatural position. In fact, the child has a relative possibility of movement, owing to the semi-rigid nature of the orientation means and of the flexible nature of the retaining means. The orientation means and the retaining means act in combination in order to restore the child's thighs to the correct abduction position, if the latter should move away therefrom. In the present case, the orientation means act mainly in the region of the lower rear side of the thighs.

FIGS. 3 and 4 show a variation of the arrangement of FIG. 1. According to this variation, the orientation means are constituted by a cushion 15. The cushion comprises an area 16 intended to be positioned and retained on the child's pelvis and two "ears" 17 and 18, respectively intended to be applied and retained in the vicinity of the lower rear side of the child's thighs, substantially in the same manner as the ends of the cross-member 3 of FIG. 1. Preferably, in its lower part, between the two ears 17 and 18, the cushion could have a convex rounded shape.

The cushion 15 is made from a semi-rigid or possibly rigid material. Advantageously, it may have a concave shape in order to constitute a hollow before or after positioning, in which the child "sits" in the abduction and bending position. The distance between the ends of the two ears 17 and 18 is substantially equal to or less than the distance between the child's two knees in the abduction position.

Furthermore, the cushion could possibly be made more rigid by cross-members, such as for example those shown diagrammatically by the dot dash line 19.

The retaining means 20 are substantially of the same type as those which were described with reference to FIG. 1. Preferably, in the vicinity of the two ears 17 and 18, they comprise projections 21 and 22. The cushion 16 can be connected to the substantially non-extensible belt 23 of the retaining means by a strip 24. Possibly, the cushion may be integrated in a pocket of the orientation means 20.

As in the preceding case, absorption means may be integrated in or associated with the orientation means and the retaining means.

FIG. 4 shows a child bound with the arrangement of FIG. 3. The method of binding as well as the method of action of the orientation means and retaining means are substantially identical to those of the arrangement illustrated in FIGS. 1 and 2.

Naturally, with respect to the afore-said, other semi-rigid orientation means acting on the rear lower side of the child's thighs, i.e. retaining the thighs from their rear side, could be used without diverging from the scope of the invention. The orientation means acting on the rear lower side of the thighs are of the ischial-sacral type.

Figure 6:
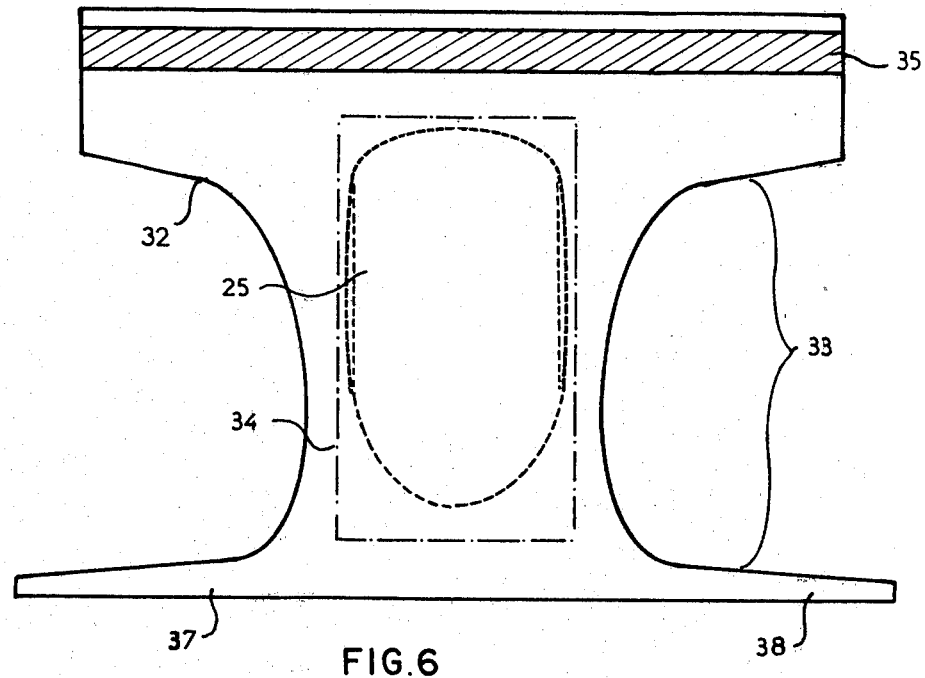
FIG. 6 shows diagrammatically the orientation means of FIG. 5 integrated in retaining means.
Figure 5:
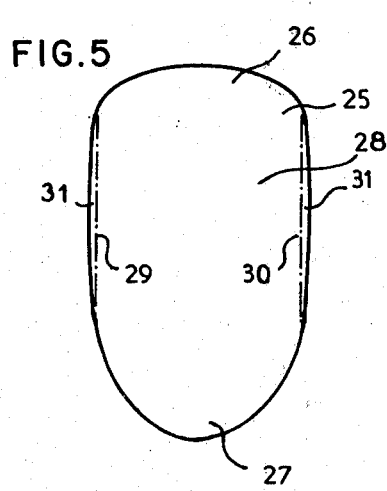
FIG. 5 shows orientation means according to another non-limiting embodiment of the invention.
Figure 7:
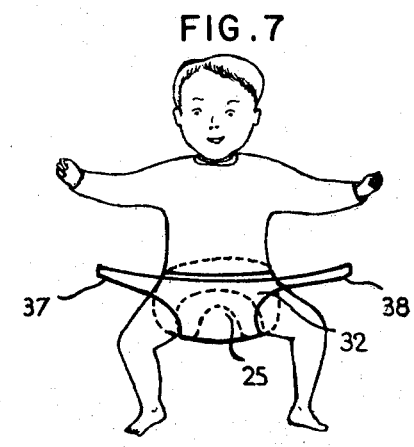
FIG. 7 shows diagrammatically a child bound with the arrangement of FIG. 6.

FIGS. 5 to 7 relate to another type of orientation means, acting mainly on the front lower side of the thighs, these means are of the ischial-pubic type.

As an example, FIG. 5 shows orientation means of this type. They are constituted by a cushion 25, of semi-rigid material possibly reinforced transversely by cross-members. Preferably, the cushion has a rounded shape in the vicinity of its upper or rear end 26 and in the vicinity of its lower front end 27. In its central region 28, its two side edges are substantially parallel.

The rear end 26 is intended to be applied against and retained on the child's pelvis, whereas the front end 27 is intended to be positioned and retained between the child's thighs, thus preventing an adduction movement of the latter semi-elastically.

The cushion 25, in position on the child, is bent longitudinally, which in its central area 28 defines two lateral passages, respectively for each thigh.

The cushion 25 is made from any suitable semi-rigid material, for example polyurethane foam. It should be noted that its longitudinal bending gives it greater transverse rigidity.

In a preferred embodiment, the side edges of the central area 28 of the cushion, which are in direct contact with the rear side of the child's thighs, comprise means for relieving hyper-pressures and facilitating the vascularisation of the childs femoral heads. These means are constituted for example by folds which are juxtaposed with respect to the side edges of the cushion. They may also be obtained from the cushion itself, by providing two lines of weakness along these side edges, which lines are shown diagrammatically in FIG. 5 by the reference numerals 29 and 30. The end side portions 31 of the cushion are thus in some way articulated in the vicinity of the lines 29 and 30 with respect to the remainder of the latter.

Other means consist of progressively reducing the thickness of the cushion in areas corresponding substantially to the areas 31. Other means are naturally possible.

FIG. 6 shows the cushion 25 of FIG. 5, integrated in retaining means 32, which are of the same type as those described with reference to the preceding figures.

The cushion 25 is positioned in the central area 33 of the retaining means. They can be stuck or welded to the latter, or integrated in a pocket, the contour of which is shown diagrammatically in FIG. 6 by the dot dash line 34. The pocket is closed or may comprise an opening on one of its sides.

As in the preceding case, the retaining means 32 of FIG. 6 comprise a substantially non-extensible belt 35 and two tapered lateral ends 37 and 38. The cushion 25 is mainly positioned in the retaining means with respect to the substantially non-extensible belt 35.

FIG. 7 shows a child bound with the arrangement illustrated in FIG. 6. The belt 35 has been closed around the child's waist, the central part 33 of the retaining means has been pulled firmly and engaged between the child's thighs, thus positioning the cushion 25 in the vicinity of the pelvis and of the front lower side of the child's thighs. It remains solely to knot the tapered lateral ends 37 and 38 on the child's back.

The orientation means, in combination with the retaining means, retain the child's thighs in the so-called abduction position, i.e. bending them at 90° approximately with respect to the pelvis and separating them by approximately 120°. It should be noted that an adduction movement of the child's thighs results in a transverse compression of the front part 27 of the cushion 25, which owing to its semi-rigid nature restores the thighs to the desired position.

As in the preceding case, absorption means could be associated with or integrated in the orientation means and retaining means illustrated in FIGS. 5 to 7.

On the other hand, in a general manner, sealing means and other means could be understood with or integrated in the arrangements which have been described. In other words, the retaining means could be of the type presently known by the name disposable nappy, all-in-one nappy, nappy pants etc.

Furthermore, the means for securing the retaining means with respect to the child could be of a different type to those which have been described. In particular, they could be of the braces type, namely of adjustable height. The retaining means could also be fixed to the lower part of a piece of clothing, such as a vest, which would comprise additional fastening means.

Another method of fastening is shown diagrammatically in FIG. 8. Advantageously, this method of fastening may be substituted for or combined with the substantially non-extensible belt and the two tapered lateral ends.

These retaining means may be constituted by two substantially non-extensible cords 39 and 40. These cords respectively form a loop 41 and 42 around each shoulder, descend along the child's sides or cross over behind the child, approximately in the vicinity of his waist. At this point they once more form a loop 43 and 44 respectively around the child's thighs and more precisely around orientation means and retaining means 45 which they press against the child's pelvis and thighs.

Possibly, a transverse cord 46 connects the loops 43 and 44 and retains them with respect to the orientation and retaining means 45. The loops 43 and 44 have an adjustable length and removable fastening means, the free end of the loops being located at the front or rear of the child. The means for fastening these loops are for example buttonholes, press studs etc.

Advantageously, the upper parts of the cords 39 and 40, comprising the loops 41 and 42 and the parts along the sides, could be integrated in a piece of clothing, in particular in the region of its seams.

Positioning of the cords 39 and 40 is effected after positioning of the retaining and orientation means. Preferably, the free ends of the loops 43 and 44 are pulled strenuously between the child's thighs and returned to the front where they are connected to the remainder of the cords.

It should be noted that the loops 43 and 44 retain the retaining and orientation means 45, but also promote the bent position of the child's thighs with respect to the pelvis.

To this end, the transverse cord 46 which connects the loops 43 and 44 and retains them, could be replaced by a rigid or semi-rigid cross-member connecting the loops 43 and 44. This cross-member would be located substantially in the region of the rear side of the thighs.

Owing to its rigidity, it maintains the spacing between the loops 43 and 44 in the position where they promote the bent position of the child's thighs with respect to the pelvis. The semi-rigid or rigid cross-member 46 itself also promotes this position and fulfils a function complementing that of the orientation means. Advantageously, it could be extended transversely beyond the loops 43 and 44 in order to increase its support surface relative to the rear side of the child's thighs.

Thus, the orientation means and retaining means do not completely oppose the child's movements, but present an "elastic" resistance to these movements and restore the thighs to the desired position "elastically," or "semi-elastically."

The function fulfilled by the cords 39 and 40 could also be fulfilled by a strip of any material, fabric, P.V.C., connected at the front and rear in an adjustable manner to the child's underwear or a piece of clothing.

The various embodiments of the napkin according to the invention, which have been described, are particularly suitable for mass manufacture, with a low cost price, in view of the nature of the means which are used. By way of example, the orientation means may be made from a material such as polyurethane foam, or for example by one or two layers of cellulose wadding reinforced by a sheet of plastics material comprising transverse reinforcing ribs.

On the other hand, the retaining means may be made from traditional materials used for napkins, such as polyvinyl chloride.

It should be noted that the materials used according to the present invention should have a natural transparency to X rays, in order to make it possible to X ray the child in position.

The napkin according to the invention, such as that described previously, is associated with absorption means. Preferably, the napkin is thrown away after each use, or after a predetermined but small number of uses, after which the orientation means no longer have sufficient rigidity.

Thus, the napkin according to the present invention may be used in place of traditional napkins and thus have a preventive nature with regard to possible abnormalities of one or both hips of a child.

Positioning of the napkin according to the invention is particularly simple and could be effected by a mother, without special medical knowledge.

On the other hand, the external appearance of the napkin according to the invention is substantially similar to traditional napkins and it may be covered by the child's clothing. Thus, in the case where the napkin is used as a curative measure, it has a clearly less unfavourable psychological effect on the people surrounding the child than that caused by currently existing specialized arrangements.

Determining the dimensions for the various means used is within the scope of a man skilled in the art. These dimensions depend mainly on the morphology of the child and his growth. The napkins according to the invention, like traditional napkins, may be sold in various sizes, corresponding respectively to lower and upper age limits of the child.

Naturally, the present description is given solely by way of example and one could adopt other embodiments of the invention without diverging from the scope of the latter.

What is claimed is:
1. A napkin for an infant designed to prevent or cure an abnormality of one or both hips, such as dysplasia, subluxation of the hip or reducible and stable luxation, by binding the infant in a napkin in the abduction position comprising:
  semi-rigid orientation means for positioning the legs of the infant in bent position at an angle of approximately 90° with respect to the pelvis and in abduction of about 60° while permitting movement of the legs, said semi-rigid orientation means being of the ischio-sacral type, and
  means for retaining said orientation means in position, said retaining means comprising flexible fabric or plastic material which is fastened around the waist of the infant and which assures maintaining the orientation means on the thighs and pelivs of the infant,
  said retaining means applying said orientation means on the pelvis and the lower rear portions of the infant's thighs and to keep the thighs flexed with respect to the pelvis, the orientation means providing a semi-elastic resistance principally to an adduction of the thighs by retaining them in, or restoring them to, the abduction position.
2. A napkin according to claim 1, in which the retaining means comprises two slender lateral extremities which can be tied at the back of the infant as well as a substantially inextensible belt.
3. A napkin according to claim 1, in which the orientation means of the ischio-sacral type comprise a transversely curved member of which two branches are positioned and maintained respectively along the lower back faces of the thighs of the retaining means.
4. A napkin according to claim 2, in which the substantially inextensible belt is closed by closing means around the waist of the infant and is connected with the orientation means by a strip defining their relative positions.
5. A napkin for an infant designed to prevent or cure an abnormality of one or both hips, such as dysplasis, subluxation of the hip or reducible and stable luxation, by binding the infant P in a napkin in the abduction position comprising;
  semi-rigid orientation means for positioning the legs of the infant in bent position at an angle of approximately 90° with respect to the pelvis and in abduction of about 60° while permitting movement of the legs, said semi-rigid orientation means being of the ischio-pubic type,
  means for retaining said orientation means in position, said retaining means comprising flexible fabric or plastic material which is fastened around the waist fo the infant and which assures maintaining the orientation means of the thighs and pelvis of the infant, said retaining means applying the orientation means on the pelvis and on the lower rear faces of the thighs bent with respect to the pelvis, the orientation means providing a semi-elastic resistance to an adducting of the thighs by pushing at the level of their lower rear faces, said semi-rigid means comprising a semi-rigid cushion which is curved longitudinally and of which the forward part is engaged between the thighs of the infant and which defines by its curvature two lateral passages for the infant's thighs respectively, the semi-rigid orientation means having along their lateral borders two zones which are more flexible than the rest of the cushion, designed to relieve hyper-pressure and to facilitate the vascularization of the femoral heads of the infant.

6. A napkin according to claim 5 in which the two more flexible lateral zones comprise borders connected with the cushion by lines of weakness.

7. A napkin according to claim 5, in which the means of the ischio-pubic type are situated in a pocket of the orientation means.

8. A napkin for an infant intended to prevent or cure an abnormality of one or both hips such as dysplasia, subluxation of the hip or reducible and stable luxation by binding the infant in a napkin in the abduction position comprising:

orientation means for holding the infants thighs at an angle approximately 90° with respect to the pelvis and approximately 120° to each other while permitting movement of the thighs, and retaining means for retaining said orientation means in position on the infant said retaining means comprising a panel of flexible fabric or plastic material of a length to extend from the infants waist, down under the crotch and back up to the waist and of a width to extend out along the infants thighs, and securing means at the upper rear end and upper front end of said panel adapted to fasten around the waist of the infant to retain said orientation means and retaining means in position, and said orientation means comprising a semi-rigid element extending transversely in a lower rear portion only of said panel in position to bear on lower rear faces of the infants thighs.

9. A napkin according to claim 8, in which said orientation means comprises an elongate cross member of semi-rigid material which extends across a lower rear portion of said panel.

10. A napkin according to claim 9, in which said cross-member is curved with a curvature corresponding to substantially to the desired angle of opening of the infants thighs.

11. A napkin according to claim 8, in which said orientation means comprises a pad of semi-rigid material.

12. A napkin according to claim 11, in which said pad is of concave shape.

13. A napkin according to claim 11 or 12 in which lateral edge portions of said pad are more flexible than the balance of said pad.

14. A napkin according to claim 8, in which said securing means comprises a belt at the upper rear end of said panel and means for fastening said belt around the waist of the infant.

15. A napkin according to claim 8 or claim 14 in which said securing means comprises two slender lateral extensions at the upper front end of said panel adapted to extend around the waist of the infant and to be fastened to one another.

16. A napkin according to claim 1, in which the means of the ischio-sacral type are situated in a pocket of the orientation means.

* * * * *